United States Patent [19]

Svegander et al.

[11] Patent Number: 4,761,610

[45] Date of Patent: Aug. 2, 1988

[54] APPARATUS FOR DETERMINING THE POSITION OF SURFACE DEFECTS OF A TEST OBJECTS WITH RESPECT TO AN EDGE THEREOF

[75] Inventors: Lennart Svegander; Bengt Törnblom, both of Västerås, Sweden

[73] Assignee: Asea AB & Tornbloms Kvalitetskontrollar, Västerås, Sweden

[21] Appl. No.: 917,067

[22] Filed: Oct. 8, 1986

[30] Foreign Application Priority Data

Oct. 18, 1985 [SE] Sweden .................... 8504912

[51] Int. Cl.⁴ .................... G01N 27/82; G01R 33/02
[52] U.S. Cl. .................... 324/227; 324/207; 324/237; 324/240; 901/9; 901/46
[58] Field of Search .............. 324/207, 208, 226, 227, 324/234, 236, 239–243, 260–262, 224, 237; 901/9, 46, 49, 50

[56] References Cited

U.S. PATENT DOCUMENTS

| | | | |
|---|---|---|---|
| 3,268,805 | 8/1966 | Normando | 324/240 |
| 3,311,819 | 3/1967 | Miller | 324/226 |
| 3,311,820 | 3/1967 | Johnson | 324/226 |
| 3,916,301 | 10/1975 | Vild et al. | 324/226 |
| 3,939,404 | 2/1976 | Tait | 324/226 X |
| 4,126,491 | 11/1978 | Kaulbson | 324/240 X |
| 4,476,434 | 10/1984 | Collins et al. | 324/226 X |
| 4,636,699 | 1/1987 | Kato | 901/49 X |
| 4,644,274 | 2/1987 | Casarcia | 324/237 X |

FOREIGN PATENT DOCUMENTS

| | | |
|---|---|---|
| 2101914 | 3/1984 | European Pat. Off. . |
| 2611539 | 9/1977 | Fed. Rep. of Germany . |
| 389916 | 5/1973 | Sweden . |

Primary Examiner—Reinhard J. Eisenzopf
Assistant Examiner—Warren S. Edmonds
Attorney, Agent, or Firm—Watson, Cole et al.

[57] ABSTRACT

Apparatus for determining the location of surface defects on a test piece of electrically conductive material by scanning the surface with at least one sensor arrangement comprising proximity sensors based on eddy current induction. The test piece may be moveable, e.g. advanced, in relation to the holder arrangement which is arranged to move the sensor arrangement in a sweeping or scanning movement from one side of the test piece to the other. The position of the edge of the test piece, is determined successively, e.g. for each scan cycle and the location of detected cracks is calculated with a starting point from the detected edge position.

9 Claims, 3 Drawing Sheets

APPARATUS FOR DETERMINING THE POSITION OF SURFACE DEFECTS OF A TEST OBJECTS WITH RESPECT TO AN EDGE THEREOF

The present invention relates to apparatus of the kind set forth in the pre-characterizing clause of claim 1.

The invention has been developed with a particular view to its application in measuring apparatus of the kind which incorporate proximity sensors based on eddy current inducement, and which are intended for measuring cracks in metal objects that present relatively broad surfaces, for example hot ingots, continuous castings, and such details as blooms, slabs, billets and the like. A particularly applicable field in this regard is the field of continuous casting, in which the solidifying steel length, here referred to as ingot, is advanced in the form of a continuous metal string. The continuous metal string, or ingot, is then cut into billets, which are subjected to further treatment by rolling or like processes. Cracks occur relatively frequently. It is essential that these cracks are detected, since they have a deleterious effect on the subsequent treatment of the billets or like details. When it is possible to discern the presence of cracks in ingots or like products, the ingots can be sorted directly into groups of ingots which contain cracks and groups of ingots which are free from cracks. The ingots which contain cracks are processed, in one way or another, in a manner to eliminate the cracks (e.g. ground with the aid of a grinding wheel), while the ingots devoid of cracks can be passed to a recipient without needing to be treated. Accordingly, although the invention can be applied advantageously in other fields, the following description will be made solely with respect to the detection of cracks in continuous casting products, using herefor a proximity sensor based on eddy current inducement. The term "test piece" as used in the aforegoing and in the following description is a general term intended to denote, for example, in addition to the aforementioned metal ingot, an extruded section, sheet metal, the surface of a molten metal bath, or any like object whose surface or surfaces is/are to be examined. The previously mentioned difficulties of detecting surface faults in hot objects are extremely prominent in the field of continuous casting, and the inventions described and illustrated in Swedish Patent Applications Ser. Nos. 7613708-2, 8206678-8 and 8302738-3, together with the present invention can be said to constitute a breakthrough in the problem of automatically detecting the presence of such cracks in a reliable and simple manner.

In order to determine the location of any cracks which may be present in a test piece, a head provided with a proximity sensor is passed backwards and forwards over the test piece to be examined, this proximity sensor preferably being a sensor based on eddy current inducement, although the use of proximity sensors based on ultrasonics, or the use of optical sensors is also possible. The test piece is moved forwards continuously in a conventional manner, substantially at right angles to the sweep direction of the sensor. The speed at which the ingot, or casting length, travels is measured conventionally with the aid of a tachometer arrangement in conjunction with the existing continuous casting apparatus. The time at which the leading edge of an ingot reaches a pre-determined location is also indicated, normally with the aid of the casting equipment.

The width of the continuously cast ingot, or test piece, may vary considerably. The width of the test piece may also vary during one and the same casting operation. Consqently, it has hitherto been difficult to establish the location of detected cracks with any degree of accuracy. The test piece is normally advanced past a proximity sensor arrangement forming part of a crack detector system located at a short distance from the path travelled by the test piece. The problem resides in the fact that while it is possible to determine accurately the momentary position of the detector arrangement and its sensor arrangement in space, the same is not normally true in the case of the test piece.

One solution to this problem is afforded by apparatus possessing the characteristic features set forth in claim 1. Further characteristics of the invention are set forth in the depending claims. By establishing the position of the leading and/or the trailing edge of the test piece under pre-determined fulfilled conditions a reference is obtained for the measuring equipment in the feed direction of movement of the test piece. A suitable method for achieving this is, for example, one of detecting the leading and/or trailing end of the object as said end passes a given position. When necessary, this position can be calculated with the aid of signals related to the speed of the test piece. The trailing edge is detected in a similar manner. Detection of the trailing edge results in the robot being guided to a home position separated from the normal measuring position.

An extremely well defined positional indication of the precise locations of detected cracks in full relationship with the test piece can be obtained with the use of measuring apparatus which sweep across the test piece in a sweep band transversely to the longitudinal axis of said test piece, at the same time as the test piece is advanced beneath, over, or to one side of the measuring equipment, and by detecting the position of the edge of the test piece in relation to said measuring equipment. Thus, one edge of the test piece is made electronically straight and the positions of respective cracks are referenced thereto.

The use of an additional measuring system is always to be avoided as far as possible, however, since additional measuring equipment will increase costs, complicate the technical solution, and require space. Accordingly, in accordance with a further development of the invention, there is utilized in this regard the pronounced change in value of at least one of the sensor signals that takes place at the transition point of measurements taken against the test piece and measurements taken against essentially empty space. When this occurs, there is produced an edge signal which indicates that the measuring and/or control arrangement has been moved out or in over the edge of the test piece.

The invention will now be described in more detail with reference to the accompanying drawings, in which FIG. 1 is a principle illustration of a first conceivable embodiment of apparatus for detecting continuously the presence of cracks in a continuously cast test piece and the position of the cracks therein;

The first conceivable embodiment of apparatus for continuously detecting the presence of cracks in a continuously cast test piece (as hereinbefore defined) is an eddy current inducing proximity sensor or sensor arrangement, which may comprise one or more proximity sensors mounted in a sensing head 1 placed on the end of an arm 2 mounted on a pivotable robot 3. The head is placed at an adapted and regulated, practically constant distance from a surface of a continuously cast test piece while the test piece is still glowing with heat. The robot 3 is swung from one side of the test piece 4 to the other by drive means provided herefor. It will be understood that in accordance with the invention a robot 3 can be positioned both beneath or on one side of the test piece, or on all sides thereof, depending on which of the surfaces of the test piece is to be examined for cracks. For the sake of simplicity, however, the following description will be curtailed to a measuring system positioned above a test piece.

When no test piece is located beneath the robot 3, there is no need for the robot to execute its scanning or pivotal movements, and the robot is preferably placed instead in a position in which the head 1 is located on one side at a position in which edge of a test piece can be expected to be found. This is due to the fact that particularly in the case of continuously casting the ingot or test piece is drawn from the tapping point of the foundry furnace with the aid of a so-called chain, which is released from the test piece once the test piece has been drawn to a given location. It is namely at this moment when examination of the leading edge of the test piece, or ingot, is first carried out, whereafter the position of the leading edge is calculated continuously on the basis of the measured forward speed of the test piece. The leading edge of the test piece is often uneven, and slightly upwardly bent, when the chain is released. Consequently, the head is not passed over the test piece until the leading edge has passed through the section over which the head will move during the first swinging movement of the robot. In other cases, when the plane of the leading edge can be expected to lie in the plane of the surface of the remainder of the test piece, the leading edge can be examined by the sensor head on the robot head. As described below, at least one of the signals produced by a multi-frequency type eddy-current inducing proximity sensor will have many different values, these values depending on whether the test piece is located directly beneath the sensor or not. Pivotal movement of the robot 3 is commenced immediately the sensor detects the arrival of a test piece, subsequent to having received a signal which denotes the absence of a test piece.

Figure 1:
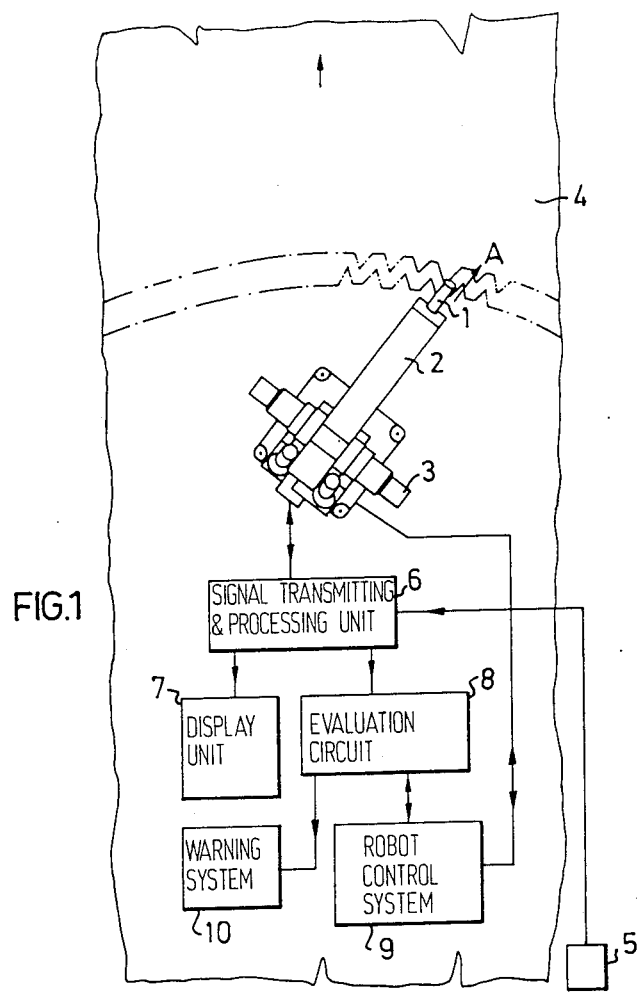

Thus, one signal provides information relating to the forward end of the test piece, while a further signal containing data relating to the speed travelled by the test piece is received from a conventional speedometer 5, often a tachometer, forming part of the continuous casting equipment. The distance between the leading end of the test piece and the position of the sensor in the forward feed direction is then measured continuously in the equipment according to the invention. The head 1 mounted on the end of the arm 2 is able to move over the test piece 4 in one continuous movement. Despite this, however, it is necessary either to arrange a number of sensors breadthwise in a particular sensor arrangement or to arrange the sensor arrangement for movement on the sensor head in a direction different to the sweep direction, in order to obtain substantially full coverage of the test piece when examining the same for cracks, since the sensor is only able to cover a relatively small area of the surface of the test piece under examination, and in order to avoid the necessity of pivoting or swinging the robot arm at an unacceptably high angular velocity. Consequently, the head 1 of the FIG. 1 embodiment is driven backwards and forwards in the direction of the arrow A. In this way, the actual sensor arrangement will move around a circular arc with superimposed transverse oscillator movement patterns over the test piece, as illustrated in the drawing. The sensor arrangement co-acts with a signal transmitting and signal processing unit 6 which, inter alia, calculates the location of detected cracks in the traverse direction, with a starting point from the position of the last detected location of one side edge of the test piece, and in the longitudinal direction with a starting point from the time at which the leading edge of the test piece was detected, while using the known forward speed of the test piece, as determined by the sensor 5. The unit 6 presents this data on a display unit or like unit 7, which is described in more detail hereinafter.

In accordance with the invention, a signal is produced from the unit 6 on a second output immediately when a radical change occurs in the value of the measuring signal or signals, such as when no eddy currents are induced in the underlying material of the test piece or when the eddy currents decrease to a marked extent, which either indicates that the sensor arrangement has been moved inwardly or outwardly over the edge of the test piece 4, or that the test piece has a crack of particular width and depth located immediately beneath the sensor arrangement. This signal is transmitted to an evaluating circuit 8, which may be constructed to carry out a so-called probability check on the signal, by ascertaining the rotational position of the robot arm, this position being given by a control circuit 9, which is normally incorporated in the robot but which for the sake of simplicity is shown separately and which interprets the signal from the unit 6 as an edge marking when the rotational position lies outside pre-given limits in one direction or the other.

If such is the case, there is produced a signal which indicates that the edge has been reached. According to the invention, this signal is used in two ways. Thus, the signal is used to obtain a positional reference or an edge position at least once during each pivotal cycle of the robot 3, and to calculate the width of the test piece for each pivot cycle. The locations of detected cracks are calculated by the unit 6, with a starting point from the edge detected at least on one side of the test piece 4 through the edge signals received from the evaluating circuit 8. The width of the test piece 4 is calculated on the basis of the two edge signals. In its second mode of use, the aforesaid signal is applied to the control circuit 9, which is constructed to stop outward movement of the arm upon receipt of said signal, movement of the arm being stopped either immediately or subsequent to the arm having moved through a given distance after receipt of the signal. Movement of the arm is then continued in another direction, either immediately or subsequent to the receipt of a control signal obtained in conjunction with the step of measuring the forward movement of the test piece.

The evaluation circuit 8 is constructed to send a signal to a warning circuit 10 upon receiving a signal from the unit 6 with the sensor arrangement located over the test piece 4.

Figure 2:
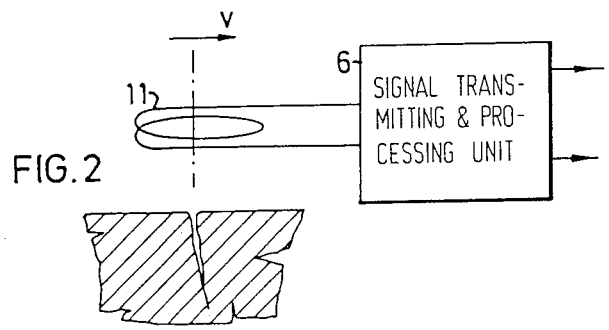
FIG. 2 illustrates an embodiment of a proximity sensor based on eddy current inducement used in accordance with the invention.

FIG. 2 illustrates an embodiment of a suitable proximity sensor based on eddy current inducement, this proximity sensor being of the kind illustrated and described in Swedish Patent Application No. 8302738-3. A coil 11 is supplied with alternating current from the signal transmitting-signal processing unit 6. The alternating current includes two mutually different frequency components fL and fH. Eddy currents of corresponding frequency content are induced in the surface of the test piece, via the inductive coupling thereto. The voltage across the coil is sensed and divided into its respective frequency components. The resultant signals are used for crack detection. One of these signals, namely the signal having the higher frequency, is used for edge marking purposes, since this signal has a high so-called lift-off-dependency, i.e. is highly dependent on the distance of the sensor from the examined surface on the test piece.

Figure 3:
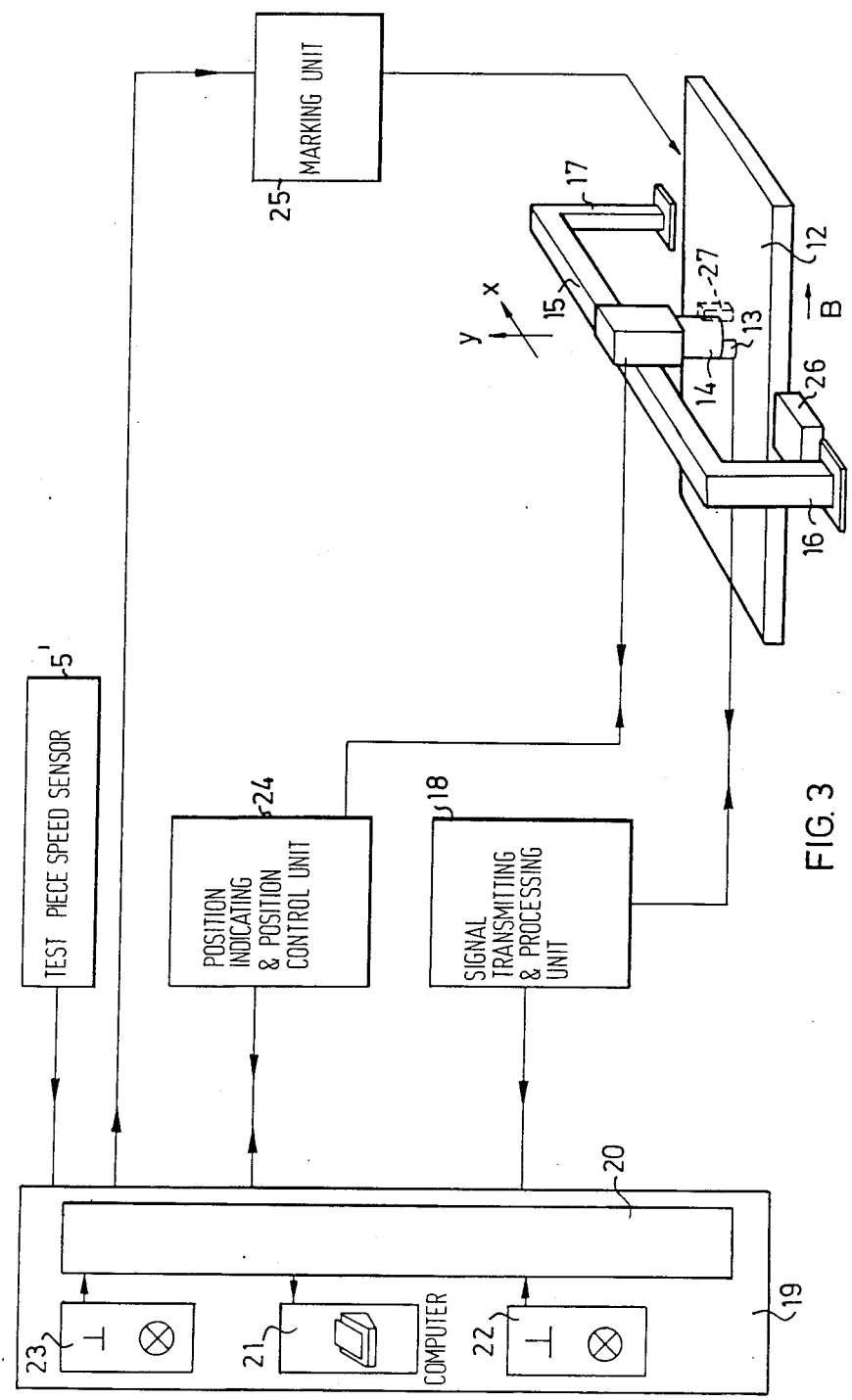
FIG. 3 is a principle illustration of a second conceivable embodiment of apparatus for continuously detecting cracks in a continuously cast test piece, and the position of the cracks therein.

FIG. 3 illustrates an arrangement for localising cracks. The test piece, here referenced 12, is moved forwards continuously in the direction of arrow B. In this embodiment a sensor arrangement 13 is mounted for rotation in a sensor head 14, which incorporates a drive motor. The sensor head 14 is mounted for guided movement along a beam 15, which is placed on pillars 16,17 and extends across the path travelled by the test piece.

Similar to that described in the aforegoing, a signal transmitting and signal processing unit 16 transmits auxiliary signals to the sensor arrangement 13 and evaluates the signal or signals obtained from said sensor arrangement.

The unit 18 is connected in turn to a control and monitoring unit 19, which includes a computer 20 or like device with peripheral equipment for presenting the results obtained, such as a printer 21 and/or an image screen or the like, a keyboard 22 for the manual insertion of data and/or some other type of data input unit 23.

The unit 19 is also supplied with a signal from a positional indicator and positional control unit 24 operating in conjunction with the sensor arrangement. The unit 24 indicates continuously the position of the sensor arrangement 13 in relation to the test piece, both in the lateral direction (x) and the vertical direction (y), and initiates adjustment of the distance to the opposing surface of the test piece, by actuating a height regulating device (not shown) in a manner to raise and lower the head 14. As indicated in the aforegoing, the momentary forward speed of the test piece is measured with the aid of a sensor 5' and the result of said measurement is delivered in the computer 20, which calculates, on the basis of said speed, the distance moved by the test piece from the time of indicating the presence of its leading edge, in a manner similar to that described with reference to FIG. 1.

The computer 20 processes the edge positions from the signals obtained from the units 18 and 24. According to the invention, the computer 20 calculates the positions of the cracks with starting point from the edge marking obtained at one edge. The width of the test piece is calculated with the aid of the edge signal obtained in respect of the other edge. Preferably, at least two memory regions are reserved in the computer 20 for width calculation purposes. At least the latest position obtained through respective edge signals on each side of the test piece is stored in these memory regions. The computer 20 calculates the width of the test piece upon receipt of each edge marking signal relating to the positional values stored in the storage elements. Thus, width measurements are calculated continuously, the results of which can be presented on the display unit 21.

Located at a specific distance from one of the pillars 17 is a marking unit 25 which, controlled by the computer 20, visibly marks, e.g. with paints, the areas where cracks are present, in the longitudinal direction of the test piece, thereby to provide visual indication of those sections of the test piece which require subsequent treatment. The marking unit 25 may alternatively be located at a different position, e.g. adjacent the sensor head 14, in which case the marking paint is applied in the immediate vicinity of the cracks.

The edge signals are also used to produce a stop signal effective to stop the head 14 moving along the beam 15. It is also possible, however, to arrange for the head 14 to continue to move along the beam through a distance corresponding, for example, to twice the radius of the circle described by the rotating sensor arrangement subsequent to applying the stop signal, therewith to achieve complete detection of the crack formation in the test piece, with commensurate processing of the signal.

As beforementioned, forward movement of the test piece is measured continuously. In order to be utilized by the position-indicating and position-control unit 24, the computer 20 calculates a forward movement measurement, which is commenced each time the sensor arrangement begins to move from one edge of the test piece to the other. When the sensor has reached said other edge and the head has stopped in response to the stop signal transmitted by the signal unit 19, the head 14 is held stationary on the beam 15, although with the sensors still rotating, until the test piece has moved through a pre-determined distance from the point at which the forward movement measurement was commenced. The head 14 is then activated to move along the beam and across the test piece in the other direction, whereafter the measuring cycle is repeated.

Due to the relatively high speed of the proximity sensor arrangement, together with its variable intersection/crossing of a crack at a plurality of locations, it is possible to establish and/or to calculate the location and orientation of the crack with a high degree of accuracy. In turn, this forms the basis for visibly marking, for example, the location, orientation and size of the crack, including its depth, which is of the greatest importance to the control of the process in question.

Figure 4:
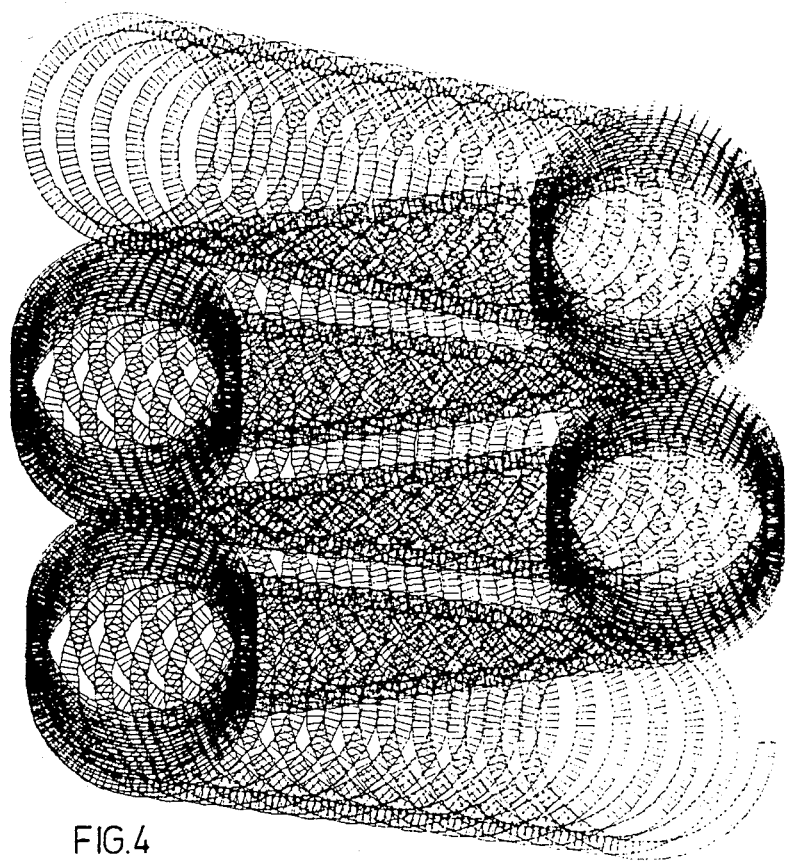
FIG. 4 and 5 illustrate examples of movement patterns carried out by the proximity sensor in FIG. 3 when passing over the test piece.

FIG. 4 is an illustration of the movement pattern described by the sensor arrangement 13 when the head 14 is moved on the beam 15 a number of times, backwards and forwards across the test piece.

The span capable of being covered by the actual sensor itself is solely equal to the breadth of the illustrated helically shaped, hatched band, although by rotating the sensor there is obtained with each scan over the test piece a covering band equal in width to the diameter of the circle described by said rotation. It will be understood that in practice the loops or turns of the helix may lie closer together than those illustrated. More specifically the turns may be so dense as to be practically tangential to one another. Thus, the rotating sensor head will pass over one and the same surface area on the test piece a number of times, although the computer 20 constantly calculates the position of the sensor arrangement in relation to said surface, partly with a starting point from one edge of the test piece, and partly with a starting point from the rotational position of the sensor arrangement 13 on the head 14 and the position of the head along the beam. The computer 20 may be programmed either to calculate the mean value of signals received for the same position in mutually different scans across the test piece, or to store the latest value received in respect of the position in question, whereupon the earlier value stored in respect of this position is erased from the memory. The use of more sophisticated data processing means for processing signals obtained in respect of one and the same position is conceivable, of course, particularly in respect of establishing the orientation of a crack.

Figure 5:
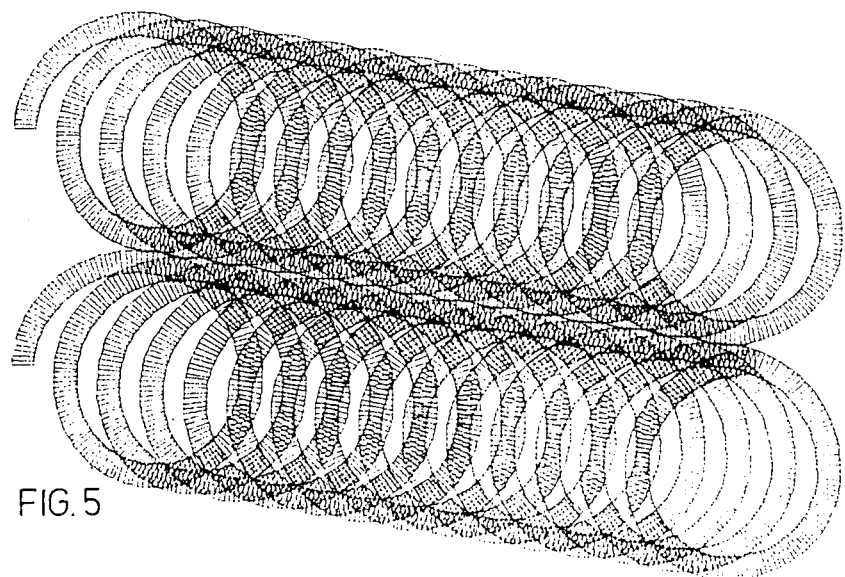

Instead of arranging for the head 14 to move reciprocatingly over the test piece for crack-detecting purposes, the head can be arranged to move rapidly back to the one edge, subsequent to having reached the other edge of the test piece and receiving the stop signal from the unit 18, and to remain stationary at said one edge until the test piece has been moved forwards through a pre-determined distance. The sensor head, together with its rotating sensor arrangement, is then again moved over the test piece in the same scanning direction as that aforementioned. The length of the aforesaid pre-determined distance may be such that the bands over which the rotating sensor arrangement scans the test piece surface with each pass are tangential to one another, or slightly overlap one another. This is illustrated in FIG. 5.

Although the invention has been described with reference to preferred embodiments thereof, it will be understood that modifications can be made within the scope of the invention. For example, the sensor head can be provided with a plurality of rotatable sensors.

The status of the equipment, e.g. its sensitivity, may need to be checked and/or measured relatively often, particularly in the case of equipment having a movement pattern as complicated as that of the arrangement according to the invention. This can be achieved by incorporating in a test piece 26, illustrated in FIG. 3, one or more reference faults, so positioned that the sensor head is able to pass readily over said fault or faults at given time points and/or when certain conditions are fulfilled, e.g. when the mean value of the sensor signal indicating a fault lies outside pre-determined limits. The test piece 26 may, for example, be placed on one side of the test piece 1 in a position over which the sensor head can readily pass.

Indication of the position of an edge of the test piece during each scanning cycle need not necessarily be carried out with the same sensor as that used to detect the presence of cracks, but may be carried out, for example, with a further sensor 27, which may be mounted on the outside of the head 14 and therefore does not rotate. When occupying the illustrated position, the rotatable sensor will pass outside the test piece through a distance equal to one radius of rotation prior to the further sensor 27 indicating the presence of an edge. When wishing to reduce the stationary dead time upon reaching an edge to the greatest possible extent, the actual sensor head 14 itself may be arranged to rotate through at least one half revolution and to be turned, prior to making a further scan across the test piece, to a position in which the further sensor 27 faces the opposing edge. It is also possible to use a totally independent edge-detecting apparatus. Whichever system is used, however, it is essential to the present invention that the detection of cracks is made with reference to at least one edge of the test piece, irrespective of how said edge is detected.

It is assumed that the apparatus, or equipment, according to the invention is arranged to co-act with grinding apparatus. The paint markings on the side of the test piece indicate the location of the cracks in the forward movement direction of the test piece with a suitable code designation. A display unit or presentation unit displays to the operator of the grinding apparatus the distance of the crack from the edge of the test piece, the operator then inserts the special code through a keyboard intended herefor. The grinding operation can be fully automated with the aid of a sensing arrangement which reads-off the marking and code on the side of the test piece and thereafter obtains the distance of the crack from the edge and the orientation and depth of the crack, or obtains the length and breadth coordinates and the depth directly from the computer 20, together with control apparatus which control the orientation of the grinding wheel and the depth to which the wheel grinds down the faulty surface of the test piece.

We claim:

1. Apparatus for examining the surface of an electrically conductive test piece for determining the location of surface defects, comprising:
   at least one sensor including at least one proximity sensor, said one sensor operating with eddy current induction for producing signals in response to the detection of surface defects;
   a holder supporting and moving said at least one sensor in a scanning movement from side to side over said surface;
   means for receiving and processing said signals;
   means for determining the position of said at least one sensor in space;
   means responsive to said at least one proximity sensor for determining the position of at least one edge of the test piece at the point where said at least one sensor travels over said edge for each scan in a first direction over said surface; and
   calculating means responsive to said means for receiving and processing and said means for determining for calculating at least one of the position and orientation of a surface defect relative to the latest determined position of said at least one edge.

2. Apparatus according to claim 1, wherein said holder moves said at least one sensor from one side of the test piece to the other in a scanning movement; and in that at least one of the sensors is held in motion, so that said at least one sensor executes movement at greater speed, independent of the scanning movement, and movement in a direction different to said scanning movement.

3. Apparatus according to claim 1 for examining the surface of a test piece which is advanced in a direction substantially transverse to the direction of movement of said holder means for determining the position of the test piece receives a passing signal when at least one of the leading edge and rear edge of the test piece passes a predetermined position; further comprising a speedometer measures the speed of the test piece and feeds the measuring signal to the means for determining the position of the test piece, said means calculating the mutual position at that time of the test piece, on the basis of the obtained applied signals.

4. Apparatus according to claim 3, wherein for each scan of said at least one sensor transversely across the test piece a part measurement of the movement of the test piece in the forward direction is carried out from the time at which said at least one sensor leaves the one side of the test piece and moves towards the other side thereof; and when said at least one sensor has reached said other side and said at least one sensor has been brought to a stationary state, this stationary state is maintained until the partial measurement indicates that the test piece has been moved through a pre-determined distance, whereafter said at least one sensor is caused to scan in the opposite direction and partial measurement of the movement of the test piece is recommenced.

5. Apparatus according to claim 1, further comprising a proximity sensor supported by said holder and responsive to a change in the signal of said means for determining the position of said at least one sensor of a character indicating a transition from measurement of the test piece and essentially empty space or vice-versa indicating that said at least one sensor has moved outwardly or inwardly over an edge of said test piece.

6. Apparatus according to claim 5, wherein said means for determining the position of the test piece obtains a signal based on a signal obtained from a moving sensor in said at least one sensor.

7. Apparatus according to claim 5, wherein means for determining the position of the test piece obtains a signal based on a signal from a stationary sensor.

8. Apparatus according to claim 5, wherein upon the occurrence of of said change in signal said means for determining the position determines the position of the sensor and initiates a check procedure to ascertain whether the sensor is located within an area in which an edge of the test piece can probably be found.

9. Apparatus according to claim 5, wherein when obtaining an edge indicating signal which indicates a transition from measuring against the test piece to measuring against essentially empty space, the means for determining the position of the test piece produces a signal which indicates that outward movement of the holder shall be stopped, either directly or after a given delay subsequent to receiving the edge indicating signal.

* * * * *

UNITED STATES PATENT AND TRADEMARK OFFICE
CERTIFICATE OF CORRECTION

PATENT NO. : 4,761,610
DATED : August 2, 1988
INVENTOR(S) : Lennart Svegander et al.

It is certified that error appears in the above-identified patent and that said Letters Patent is hereby corrected as shown below:

Title page:

Assignee's name should read as follows:

[73] Assignee: ASEA AB & TÖRNBLOMS KVALITETSKONTROLL AB

Signed and Sealed this

Twenty-first Day of February, 1989

*Attest:*

DONALD J. QUIGG

*Attesting Officer*  *Commissioner of Patents and Trademarks*